(12) United States Patent
Greenberg et al.

(10) Patent No.: US 8,920,345 B2
(45) Date of Patent: Dec. 30, 2014

(54) SYSTEM AND APPARATUS FOR CONTINUOUS MONITORING OF MOVEMENT DISORDERS

(75) Inventors: Andrew Greenberg, Portland, OR (US); James McNames, Portland, OR (US); Pedro Mateo Riobo Aboy, Beaverton, OR (US)

(73) Assignee: APDM, Inc., Portland, OR (US)

( * ) Notice: Subject to any disclaimer, the term of this patent is extended or adjusted under 35 U.S.C. 154(b) by 874 days.

(21) Appl. No.: 12/632,778

(22) Filed: Dec. 7, 2009

(65) Prior Publication Data

US 2010/0145236 A1    Jun. 10, 2010

Related U.S. Application Data

(60) Provisional application No. 61/120,485, filed on Dec. 7, 2008.

(51) Int. Cl.
*A61B 5/103* (2006.01)
*A61B 5/11* (2006.01)
*A61B 5/00* (2006.01)

(52) U.S. Cl.
CPC ............. *A61B 5/1101* (2013.01); *A61B 5/0002* (2013.01); *A61B 2560/0475* (2013.01); *A61B 2562/0219* (2013.01); *A61B 2560/029* (2013.01); *A61B 2560/0456* (2013.01)
USPC ....................................................... 600/595

(58) Field of Classification Search
USPC ....................................................... 600/595
See application file for complete search history.

(56) References Cited

U.S. PATENT DOCUMENTS

| 4,117,834 | A | 10/1978 | Mc Partland |
| 4,306,291 | A | 12/1981 | Zilm |
| 4,353,375 | A | 10/1982 | Colburn |
| 5,293,879 | A | 3/1994 | Vonk |
| 5,562,104 | A | 10/1996 | Hochberg |
| 6,343,208 | B1 * | 1/2002 | Ying .......................... 455/575.7 |
| 7,089,148 | B1 | 8/2006 | Bachmann |
| 7,141,026 | B2 | 11/2006 | Aminian |

(Continued)

OTHER PUBLICATIONS

Sadat et al. "Low-Power CMOS Wireless MEMS Motion Sensor for Physiological Activity Monitoring" 2005, IEEE pp. 2539-2550.*

*Primary Examiner* — Max Hindenburg
*Assistant Examiner* — Renee Danega
(74) *Attorney, Agent, or Firm* — Mateo Aboy; Aboy & Associates PC

(57) ABSTRACT

Disclosed embodiments include a complete system and platform which allows for continuous monitoring of movement disorders during normal daily activities in the clinic, home, and other normal daily environments. The system comprises: 1) a wearable apparatus for continuous monitoring of movement disorders, 2) a docking station, 3) a web server, and 4) methods for statistical analysis that generate movement impairment measures. Disclosed embodiments include a wearable movement monitoring apparatus comprising of (a) a sensor module including a plurality of low power microelectromechanical systems kinematics sensors; (b) a microprocessor module including a low power microcontroller configured for device control, device status, and device communication; (c) a data storage module including a solid state local storage medium; (d) a wireless communication module including a low power surface mount transceiver and an integrated antenna; and (e) a power and docking module including a battery, an energy charging regulator circuit, and a docking connector.

19 Claims, 2 Drawing Sheets

(56) References Cited

U.S. PATENT DOCUMENTS

| | | |
|---|---|---|
| 7,210,240 B2 | 5/2007 | Townsend |
| 7,395,181 B2 | 7/2008 | Foxlin |
| 7,670,295 B2 * | 3/2010 | Sackner et al. ............... 600/483 |
| D614,979 S | 5/2010 | McNames |
| 7,927,253 B2 * | 4/2011 | Vincent et al. .................... 482/9 |
| 2004/0015103 A1 | 1/2004 | Aminian |
| 2005/0010139 A1 | 1/2005 | Aminian |
| 2005/0234309 A1 | 10/2005 | Klapper |
| 2007/0032748 A1 | 2/2007 | Mcneil |
| 2007/0236180 A1 * | 10/2007 | Rodgers ........................ 320/115 |
| 2007/0249968 A1 | 10/2007 | Miesel |
| 2007/0250286 A1 * | 10/2007 | Duncan et al. ................ 702/139 |
| 2007/0255118 A1 | 11/2007 | Miesel |
| 2008/0053253 A1 * | 3/2008 | Moore et al. ................. 73/865.4 |
| 2008/0284650 A1 * | 11/2008 | MacIntosh et al. ...... 342/357.14 |
| 2008/0285805 A1 | 11/2008 | Luinge |
| 2009/0281830 A1 | 11/2009 | McNames |
| 2010/0030119 A1 | 2/2010 | McNames |
| 2010/0076348 A1 | 3/2010 | McNames |
| 2010/0145236 A1 | 6/2010 | Greenberg |
| 2010/0305437 A1 * | 12/2010 | Liebschner et al. .......... 600/437 |

* cited by examiner

SYSTEM AND APPARATUS FOR CONTINUOUS MONITORING OF MOVEMENT DISORDERS

CROSS-REFERENCE TO RELATED APPLICATIONS

This application claims the benefit of U.S. Provisional Application No. 61/120,485 filed on 2008 Dec. 7 by the present inventors, which is incorporated herein by reference.

FEDERALLY SPONSORED RESEARCH

Not Applicable.

SEQUENCE LISTING OR PROGRAM

Not Applicable.

BACKGROUND

1. Field of Invention

This invention relates to the physiologic monitoring of movement. Specifically, it relates to systems and devices for continuous and ambulatory measurement of the symptoms of movement disorders using wearable monitoring devices.

2. Prior Related Art

State of the art movement disorder monitors employ inertial sensors, such as accelerometers and gyroscopes, to measure position, velocity and acceleration of the subject's limbs and trunk. Current monitors fall into two classes, namely activity monitors and inertial monitors, both of which have disadvantages and limitations that make them incapable of continuous monitoring of movement disorders in ambulatory settings.

Activity monitors, such as in U.S. Pat. No. 4,353,375, collect low frequency and low resolution samples of the subject's gross activity for days to weeks at a time. These monitors are usually small, unobtrusive devices resembling watches or brooches which are worn by the subject for long periods of time such as days or weeks outside of the clinical setting. They measure movement using low quality inertial sensors at low sampling frequencies, and usually measure only a few degrees of freedom of motion instead of all six possible degrees of freedom of motion. The low quality measurements are stored in data storage on-board the device which is later downloaded and analyzed. While they are useful for recording the gross activity levels of the subject, and they may be comfortable and unobtrusive enough to be worn by the subject for longs periods of time, they are only useful in measuring non-subtle symptoms of movement disorders such as activity versus rest cycles. Subtle symptoms, such as symptom onset and decline, or non-obvious symptoms such as bradykinesia, can not be measured by these devices. These devices, also known as actigraphers, typically measure movement counts per minute which make even simple determinations such as determining the wake-up time challenging. Consequently, actigraphers are inappropriate for continuous ambulatory monitoring of movement disorders such as in Parkinson's disease.

Inertial monitors, such as in U.S. Pat. No. 5,293,879, collect high frequency, high resolution samples of the subject's movements for short periods of time. These devices are larger and more obtrusive, resembling small boxes which are worn by the subject for short periods of time such as hours, or at most, a day, and usually in clinical settings. They measure movement using high quality inertial sensors, and usually include all six degrees of freedom of motion (three linear axes and three rotational axes). Inertial monitors may store the inertial measurements in the device for later analysis, or they may use telemetry radios to wirelessly transmit the measurements in real-time to a nearby computer or recording device. These devices are useful for measuring all symptoms of movement disorders, but because of their larger, obtrusive size and short operational times, are not useful for measuring symptoms outside of clinical settings or for long periods of time.

Movement disorder monitoring can be enhanced by monitoring multiple locations on a subject at the same time. Current systems either do not synchronize their measurements, or require wires to synchronize sampling. Additionally, current movement disorder monitoring devices also lack aiding sensors, such as absolute measures of position.

Movement monitoring devices and systems that overcome challenges of physical size, power consumption, and wireless synchronization are currently unavailable and have significant potential in numerous applications including clinical practice and research. For instance, in current medical practice and clinical trials, Parkinson's disease (PD) is assessed briefly using rating scales or less formal examinations. In some studies patient diaries are used as a type of patient reported outcome (PRO) to determine the effectiveness of therapy. Current methods of motor system assessment for PD are inadequate because they are intermittent, subjective, and have poor sensitivity. Presently motor symptoms are diagnosed and assessed during a brief clinical evaluation performed by a primary care physician or neurologist every 3-6 months. Some clinicians use scales such as the Unified Parkinson's Disease Rating Scale (UPDRS). This scale has been the most rigorously and thoroughly evaluated for its clinimetric properties and especially its reliability and validity. The interrater reliability has ranged from "moderate" to "excellent". The UPDRS and other clinical rating scales are coarse, subjective, momentary, stressful to the patient, and insensitive to subtle changes in the patient's motor state. These scales can only be applied in clinical settings by trained clinicians. The value of these scales is limited because each patient's motor state varies continuously throughout the day and can be altered by diet, activity, stress, quality of sleep, or anxiety. In particular, dyskinesias are often at their worst during normal daily activities and may have a diurnal pattern. Medical devices that have been designed to more precisely and objectively measure the motor symptoms also have this limitation. Patient diaries and other methods of self reporting are sometimes used to determine patients' motor condition throughout the day, but these are often inaccurate, incomplete, cumbersome, and difficult to interpret. These methods are also susceptible to selection, perceptual, and recall bias. Patients generally have poor consistency and validity at assessing the clinical severity of their impairment. Patients with mild or moderate dyskinesia may be unaware of their impairment and may have poor recall. However, patients may be able to accurately monitor their overall disability.

Currently, the most common and accurate method of tracking movement is based on optical motion analysis systems. However, these systems are expensive, can only measure movements in a restricted laboratory space, and cannot be used to observe patients at home.

Current inertial monitoring systems can be divided into three categories: computer-tethered, unit-tethered, and untethered. Computer-tethered devices connect the sensor directly to a computer. One of the best systems in this category is MotionNode (GLI Interactive LLC, Seattle). These systems are not practical for home settings. Unit-tethered systems connect the sensors to a central recording unit that is typically worn around the waist. This unit typically houses the memory, batteries, and wireless communications circuits. Currently, these systems are the most widely available and are the most common in previous studies. One of the best systems in this category is the Xbus kit (Xsens, Netherlands). This system includes up to five sensors, each with high-performance, triaxial accelerometers, gyroscopes, and magnetometers. The system can operate continuously and wirelessly stream data via Bluetooth to a laptop for over 3 h at distances up to 100 m. However the system is too cumbersome and difficult to use in a home study due to the wires connecting the sensors and central recording unit, the battery life is too short, and the interconnecting wires may be hazardous during normal daily activities. The typical untethered system combines the batteries, memory, and sensors in single stand-alone units. The only wireless untethered systems reported in the literature are "activity monitors," which measure the coarse degree of activity at intervals of 1-60 s, typically with a wrist-worn device that contains a single-axis accelerometer. These devices are sometimes called actigraphs or actometers. Most of these devices only report activity counts, which are a measure of how frequently the acceleration exceeds a threshold. Some custom activity monitors directly compute specific metrics of motor impairment, such as tremor. A few studies have shown that activity monitors worn over 5-10 days could detect on/off fluctuations, decreased activity from hypokinesia, and increased activity associated with dyskinesia. However, typical activity monitors cannot distinguish between motor activity caused by voluntary movement, tremor, or dyskinesia. They do not have sufficient bandwidth, memory, or sensors for precise monitoring of motor impairment in PD. They also cannot distinguish between periods of hypokinesia and naps.

Recently, Cleveland Medical Devices (Cleveland, Ohio) introduced two untethered systems, the KinetiSense and Kinesia devices. These systems include triaxial accelerometers and gyroscopes with bandwidths of 0-15 Hz, but lack magnetometers. Although large, the central recording units could to be worn on the wrist. The sensor and recording unit can be connected to form a single unit. This devices can record data continuously and store it on an on-board memory for up to 12 h. However, 1) the due to their size it is difficult for several of these devices to be used at the same time (e.g. wrist, ankle, waits, trunk), 2) the storage capability is limited to a single day and consequently it is difficult to conduct multiple day studies, and 3) the devices are not synchronized.

Movement monitoring devices and systems that overcome the challenges of 1) physical size (volume), 2) power consumption, 3) wireless synchronization, 4) wireless connectivity, 5) automatic calibration, and 6) noise floor; are currently unavailable and have significant potential in numerous applications including clinical practice and research. Finally, the limited solutions currently available are device-centric and do not include a complete platform to perform collection, monitoring, uploading, analysis, and reporting.

SUMMARY

Disclosed embodiments include a a wearable movement monitoring apparatus comprising of (a) a sensor module comprising a plurality of low power solid state kinematics sensors; (b) a microprocessor module comprising a low power microcontroller configured for device control, device status, and device communication; (c) a data storage module comprising a solid state local storage medium; (d) a wireless communication module comprising a low power surface mount transceiver and an integrated antenna; and (e) a power and docking module comprising a battery, an energy charging regulator circuit, and a docking connector.

DETAILED DESCRIPTION

A. System Components

Figure 1:
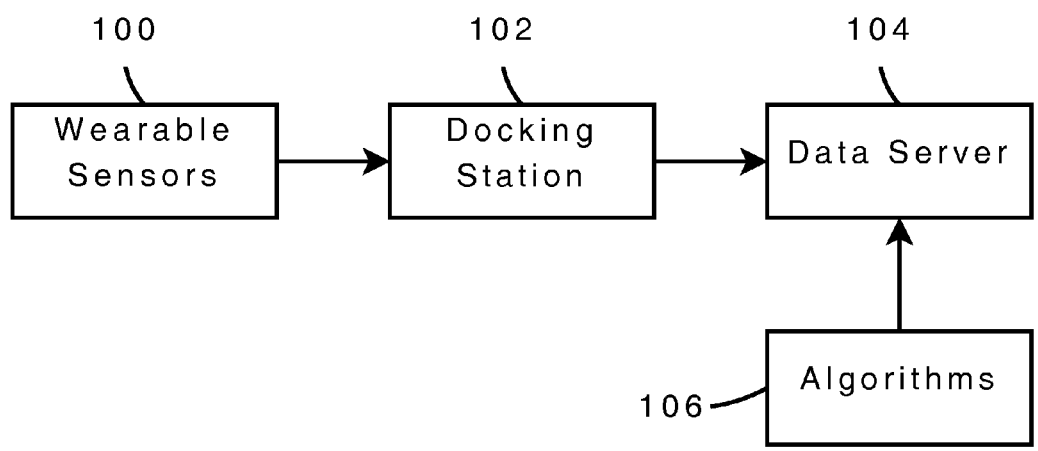
FIG. 1 illustrates a block diagram representing the basic components of an embodiment of the general systems for continuous and objective movement monitoring.

According to one embodiment, as shown in FIG. 1 the system for continuous ambulatory monitoring of movement disorders comprises: one or more wearable devices 100, one or more docking stations 102 connected to a plurality of access points, one or more data servers 104, and a plurality of statistical and signal processing analysis methods 106 to process the movement data collected by the wearable devices and generate a plurality movement metrics.

B. Wearable Devices: Movement Monitors

According to one embodiment the wearable movement monitor 100 is a lightweight device (<100 g) comprising (a) a sensor module comprising a plurality of low power (<50 mW) solid state and micro-electromechanical systems kinematics sensors; (b) a microprocessor module comprising a low power (<50 mW) microcontroller configured for device control, device status, and device communication; (c) a data storage module comprising a solid state local storage medium; (d) a wireless communication module comprising a low power (<50 mW) surface mount transceiver and an integrated antenna; and (e) a power and docking module comprising a battery, an energy charging regulator circuit, and a docking connector. In one embodiment, the micro-electromechanical systems kinematics sensors include a plurality of solid-state, surface mount, low power, low noise inertial sensors including a plurality of accelerometers and gyroscopes, as well as a solid-state, surface mount, low power, low noise, Gigantic Magneto-Resistance (GMR) magnetometers. In a particular embodiment, the solid state local storage medium is substantially equivalent to a high capacity SD card (>4 GB) in order to enable for multi-day (>2 days) local storage of movement monitoring data at high frequencies sampling frequencies (>20 Hz). In one embodiment, the communication module is designed to communicate with a plurality of wearable movement monitors (peer-to-peer communication) in order to synchronize the monitors, and to communicate with a host computer (peer-to-host communication) to transmit sensor data, uses a bidirectional groundplane PCB patch antenna, and accepts transmissions from a plurality of beacons to calculate the device location. In one embodiment, the power and docking module includes an external connector to access external power and provide high speed communication with an external docking station, the energy charging regulator circuit is a solid state integrated circuit charger such as a linear Lithium Ion Polymer battery charger IC and said battery is a Lithium Ion Polymer battery, and Lithium Ion Polymer battery can be selected for a particular application as a function of its mAHr characteristics (e.g. 450 mAHr or 50 mAHr).

According to another embodiment, the wearable movement monitoring apparatus 100 further comprises an external movement monitoring system comprising: (a) an external docking station for re-charging the wearable movement monitoring apparatus, storing movement data, and transmitting the movement data to a plurality of receiver devices, (b) a plurality of wireless transceiver access points for wireless transmission of the movement data to a plurality of receiver devices, and (c) a web-enabled server computer including a clinical data management and analysis system for storing, sharing, analyzing, and visualizing movement data using a plurality of statistical signal processing methods.

According to a preferred embodiment the movement monitor apparatus 100 is a lightweight, low-power, low noise, wireless wearable device with the following characteristics: 1) weight of 22 g, 2) sampling frequency of 128 Hz, 3) wireless synchronization, 4) 14 bit resolution, 5) three-axis MEMS accelerometers (user configurable from ±2 g to ±6 g), 6) three-axis MEMS gyroscopes with a ±1500 deg/s range, 7) three-axis magnetometers with a ±6 Gauss range, 7) automatically calibrated, 8) over 16 hours of operation per charge, and 9) over 20 days of onboard storage capacity. According to a preferred embodiment the device 100 includes solid state, low-power, low-noise sensors as follows: accelerometer (0.001 m/s$^2$/sqr(Hz)), XY gyroscope (p0.01 deg/s/sqrt(Hz)), z Gyroscope (0.1 deg/s/sqrt(Hz)), and magnetometer (170 nT/sqrt(Hz)).

According to one embodiment, the wearable devices or apparatus 100 are compact movement monitoring devices that continuously record data from embedded sensors. The sensors 100 may be worn at any convenient location on the body that can monitor impaired movement. Convenient locations include the wrists, ankles, trunk, and waist. In one to one embodiment, the sensors include one or more channels of electromyography, accelerometers, gyroscopes, magnetometers, and other MEMS sensors that can be used to monitor movement. The wearable sensors 100 have sufficient memory and battery life to continuously record inertial data throughout the day from the moment subjects wake up until they go to sleep at night, typically 18 hours or more. In one particular embodiment designed for continuous monitoring of movement during daily activities the device uses a storage element substantially equivalent to an SD card to store movement data for extended periods of time (e.g. 1 month). The sensors 100 automatically start recording when they are removed from the docking station. In one embodiment, there is no need for the user to turn them on or off.

Figure 2:
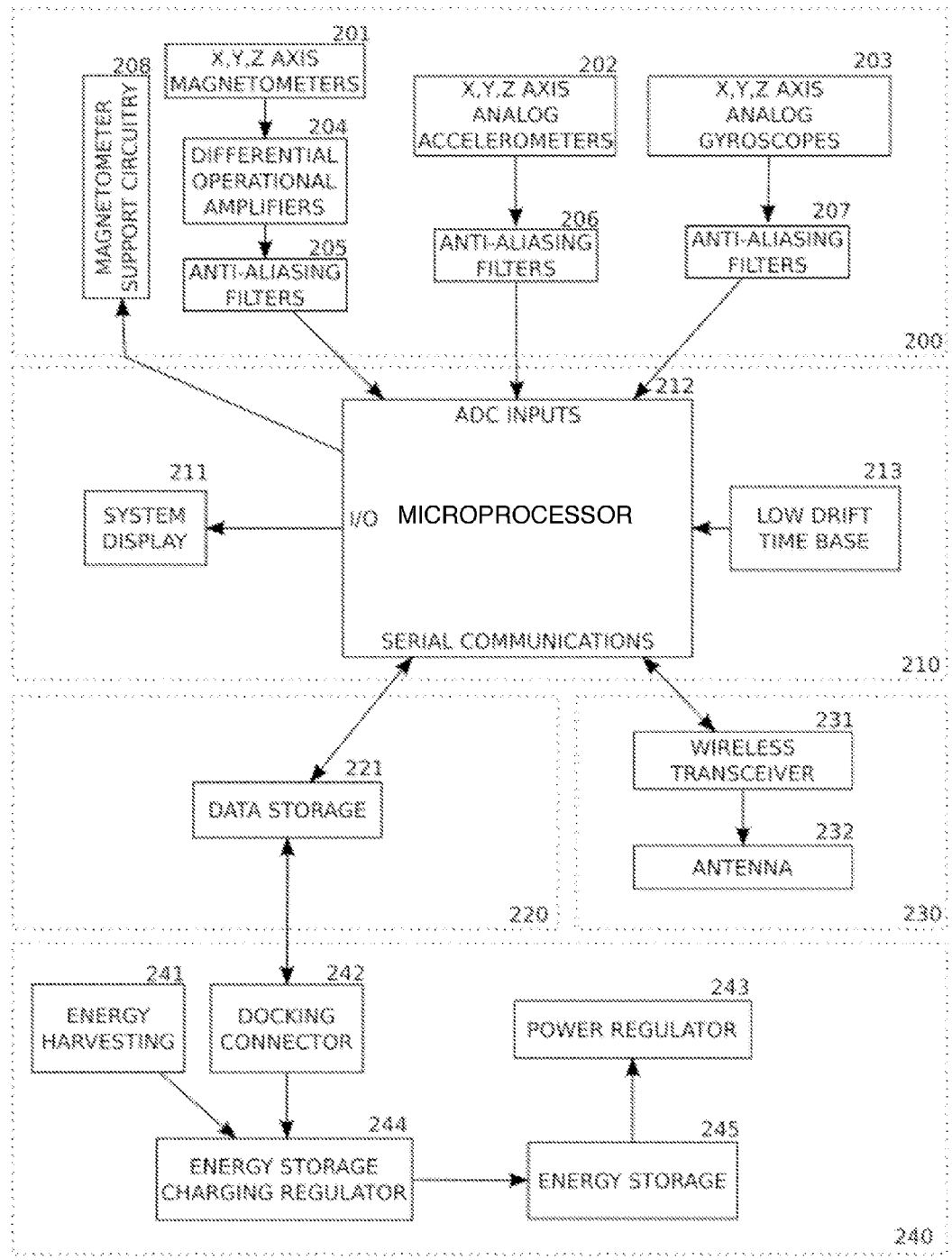
FIG. 2 illustrates a detailed diagram of the basic components and interconnections of an embodiment of the wearable apparatus for continuous and objective movement monitoring.

According to one embodiment, the wearable devices 100 include the components and interconnections detailed in FIG. 2: a sensor module 200, a microprocessor module 210, a data storage module 221, a wireless communication module 230, and a power and docking module 243. An embodiment of each of these modules comprising the apparatus for continuous and objective monitoring of movement disorders is described in detail below. In addition to movement monitoring in clinical applications such as movement disorders, the embodiments disclosed can be use to characterize movement in a plurality of application areas including continuous movement monitoring, activity monitoring, biomechanics, sports science, motion research, human movement analysis, orientation tracking, animation, virtual reality, ergonomics, and inertial guidance for navigation, robots and unmanned vehicles.

B.1. Sensor Module

The sensor module 200 in FIG. 2 contains the motion sensors necessary to characterize the symptoms of movement disorders. Three of these sensors are low noise accelerometers 202. According to one embodiment, the accelerometers are off-the-shelf, commercially available Micro-ElectroMechanical Systems (MEMS) acceleration sensors in small surface-mount packages, such as the STMicro LIS344AHL. In other embodiments, the acceleration sensors are custom made MEMS accelerometers. The accelerometers are arranged in three orthogonal axes either on a single multi-axis device, or by using one or more separate sensors in different mounting configurations. According to one embodiment, the output of the accelerometers 202 is an analog signal. This analog signal needs to be filtered to remove high frequency components by anti-aliasing filters 206, and then sampled by the analog-to-digital (ADC) peripheral inputs of the microprocessor 212. According to one embodiment the anti-aliasing filters are single pole RC low-pass filters that require a high sampling frequency; in another, they are operational amplifiers with multiple-pole low pass filters that may use a slower sampling frequency. In other embodiments, the device includes an analog interface circuit (AIC) with a programmable anti-aliasing filter. According to another embodiment, the output of the accelerometers is digital, in which case the sensor must be configured for the correct gain and bandwidth and sampled at the appropriate rate to by the microprocessor 212.

The next three sensors in the the sensor module 200 are solid state, low noise rate gyroscopes 203. In one embodiment, the accelerometers are off-the-shelf, commercially available Micro-ElectroMechanical Systems (MEMS) rotational sensors in small surface-mount packages, such as a the Invensense IDG-650 and the Epson Toyocomm XV-3500CBY. In other embodiments are custom made MEMS. The gyroscopes are arranged in three orthogonal axes either on a single multi-axis device, or by using one or more separate sensors in different mounting configurations. According to one embodiment, the output of the gyroscopes 203 is an analog signal. This analog signal needs to be filtered to remove high frequency components by anti-aliasing filters 207, and then sample by the analog-to-digital (ADC) peripheral inputs of the microprocessor 212. According to one embodiment the anti-aliasing filters are single pole RC low-pass filters that require a high sampling frequency; in another, they are operational amplifiers with multiple-pole low pass filters that may use a slower sampling frequency. In other embodiments, the device includes an analog interface circuit (AIC) with a programmable anti-aliasing filter. According to another embodiment, the output of the gyroscopes is digital, in which case the sensor must be configured for the correct gain and bandwidth and sampled at the appropriate rate to by the microprocessor 212.

The sensor module 200 also contains one ore more aiding sensors. According to one embodiment, an aiding system is a three axis magnetometer 201. By sensing the local magnetic field, the magnetometer is able to record the device's two axes of absolute attitude relative to the local magnetic field which can aid correcting drift in other inertial sensors such as the gyroscopes 203. In one embodiment, the magnetometer sensors are off-the-shelf, low noise, solid-state, GMR magnetometer in small surface-mount packages such as the Honeywell HMC1043. In other embodiments are custom made MEMS. The magnetometers are arranged in three orthogonal axes either on a single multi-axis device, or by using one or more separate sensors in different mounting configurations. According to one embodiment, the output of each magnetometer 203 is an analog signal from two GMR magnetometers arranged in a Wheatstone bridge configuration, which requires a differential operational amplifier 204 to amplify the signal and an anti-aliasing filter 207 to remove high frequency components. These amplified, anti-aliased filters are then sampled by the analog-to-digital (ADC) peripheral inputs of the microprocessor 212. According to one embodiment the anti-aliasing filters are single pole RC low-pass filters that require a high sampling frequency; in another, they are operational amplifiers with multiple-pole low pass filters that may have a slower sampling frequency. In other embodiments, the device includes an analog interface circuit (AIC) with a programmable anti-aliasing filter. According to another embodiment, the output of the gyroscopes is digital, in which case the sensor must be configured for the correct gain and bandwidth and sampled at the appropriate rate to by the microprocessor 212. Unlike conventional MEMS inertial sensors, magnetometer sensors may need considerable support circuitry 208, which in one embodiment include such functions as temperature compensation of the Wheatstone bridge through controlling the bridge current, and low frequency magnetic domain toggling to identify offsets through the use of pulsed set/reset coils.

Although not specifically depicted in the sensor module 200, other aiding sensors could be added. In one embodiment, a Global Positioning System Satellite Receiver is added in order to give absolute geodetic position of the device. In another embodiment, a barometric altimeter is added to give an absolute indication of the vertical altitude of the device. In another embodiment, beacons consisting of devices using the same wireless transceiver 231 could also tag specific locations by recording the ID of the beacon.

B.2. Microprocessor Module

The microprocessor module 210 in FIG. 2 is responsible for device control, device status, as well as local data and communication processing. The microprocessor 212 may indicate the device's status on some kind of visual or auditory display 211 on the device. In one embodiment, the display is a a red-green-blue (RGB) light emitting diode (LED). In another embodiment, a small LCD panel is used to display information, such as the time of day, system status such as battery charge level and data storage level, and a medication reminder for subjects who require medication for to treat their movement disorder. In another embodiment, the medication reminder is a gentle vibration, auditory, or visual cue that reminds subjects to take any necessary treatment or perform symptom measurement tasks.

According to one embodiment, the microprocessor 212 is a low power microcontroller such as the Texas Instruments MSP430FG4618. The microprocessor coordinates the sampling of sensors, data processing, data storage, communications, and synchronization across multiple devices. The microprocessor should be a lower power device with enough computational resources (e.g. 20 MIPS) and input/output resources (more than 20 general purpose input/output lines, 12 analog-to-digital converter inputs, more than two serial communication ports, etc) to interface to other modules.

The microprocessor is clocked by a low drift time base 213 in order to accurately maintain both a real time clock (RTC) and to minimize drift in the synchronous sampling across multiple devices on one subject over long periods of time. In one embodiment, the low drift time base is a temperature compensated crystal oscillator (CTXO) such as the Epson TG3530SA. In another embodiment, the time base is a standard microprocessor crystal with custom temperature compensation using the digital-to-analog converter of the microprocessor 212. Using a CTXO instead of a standard microprocessor crystal also minimizes power consumed by the wireless communication module 230 since the frequency necessary to re-synchronize devices is reduced.

B.3. Data Storage Module

The data storage module 221 stores the measurements from the sensors 200 and status of the device (such as the energy storage device's 245 charge level) locally on the device. It is especially designed to support studies involving multi-day continuous movement monitoring. In one embodiment, the device is capable of storing movement data at a sampling frequency of 128 Hz for over 20 days. In one embodiment, the local storage is Flash memory soldered to the device's printed circuit board. In another embodiment, a high capacity Flash card, such as a >4 GB MicroSD card, is used with a high speed synchronous serial port (SPI) from the microprocessor 212 to minimize wire complexity and to enable a standard protocol to hand off to a host computer as necessary. In another embodiment, the data storage module is greatly reduced, or even unnecessary, because data is streamed directly off the device using the wireless communication module 230.

B.4. Wireless Communication Module

The wireless communication module 230 allows the device to communicate to other devices (peer-to-peer), to a host computer (peer-to-host) and to listen to other data such as wireless beacons. The wireless communication module serves multiple functions: it broadcasts data from the device's inertial sensors 200 to a computer or other recording device, it synchronizes sampling rate across multiple devices through a sampling time synchronization protocol, and allows for configuring the devices behavior (i.e. mode of operation). Another use for the wireless communication module is to listen for transmissions from beacons which informs the device about its current location (e.g. bathroom, kitchen, car, workplace, etc). In one embodiment, the communication protocol is a industry standard protocol such as Bluetooth, ZigBEE, WiFi or substantially equivalent protocol. In another embodiment, it is a custom communication protocol based on a physical layer transceiver chip.

One embodiment of the wireless communication module consists of a low power, 2.4 GHz surface mount wireless transceiver 231, such as the Nordic Semiconductor nRF24L01+. The wireless transceiver uses a small on-board antenna 232, such as a chip antenna like the gigaNOVA Mica antenna for both transmitting and receiving wireless communications. In another embodiment, the antenna is a ground-plane PCB patch antenna. In one embodiment, the wireless transceiver 231 uses a high speed synchronous serial port, such as the serial peripheral interface (SPI), to communicate with the host microprocessor 212. In another embodiment, the wireless transceiver is built into the microprocessor as a peripheral. In another embodiment, the wireless transceiver uses skin conduction to create a Personal Area Network (PAN) instead of a broadcast radio. Another embodiment uses light, such as infrared light, as a wireless communication system like the industry standard IRDA. In this last embodiment, the antenna 232 would be an optical transceiver.

B.5. Power and Docking Module

The power and docking module 240 provides external power, power regulation, and external data connections to the device. One aspect of the power and docking module is the docking connector 242 which provides an external connector to access external power and provide high speed communication with the docking station, and thus to a computer or other recording device. One embodiment of the connector 242 is the Hirose ST60 series connector which provides enough connections for both power and complete hand off of the data storage module 220 for extremely high throughput downloading of data. In another embodiment, the docking connector is completely wireless, and provides inductive wireless power transmission for external power and a local high speed wireless data channel.

Most energy storage devices much be carefully charged, so the energy storage charging regulator 244 must carefully charge the energy storage device 245. In one embodiment, the energy storage charger is a linear Lithium Ion Polymer battery charger IC such as the Microchip MCP73833, or substantially equivalent integrated circuit. In another embodiment, it is a switching battery charge IC. In another embodiment, the microprocessor 212 measures the battery capacity and controls the energy storage device's charge directly.

The energy storage mechanism 245 is in one embodiment a Lithium Ion Polymer battery. Other embodiments involve other energy storage mechanism, such as super capacitors or other battery chemistries. The Lithium ion polymer battery should be sized appropriately to be as small as possible for the comfort of the subject wearing the device, yet still contain enough stored energy to power the system for a sufficiently long period of time. In one embodiment, a 450 mAHr battery is used to enable the device to last 24 hours and thus be usable for a full day before recharging is required. In another embodiment, a smaller 50 mAHr battery is used to minimize the device size for short term clinical use.

A power regulator 243 must be used to regulate the power coming from the energy storage device. According to one embodiment, a simple voltage regulator such as the Texas Instruments TPS79901 or equivalent, prepares the energy storage device's power for use by the other modules (200, 210,210,220,230).

Device operation can be extended or performance improved by harvesting energy from the local environment. One embodiment of an energy harvesting device 241 is a small solar panel on the outside of the device. Another is a small kinetic generator using piezoelectric materials to generate voltage. A third uses heat differences between the subject's skin and the ambient air temperature.

B.6. External Docking Station

According to one embodiment, in order to facilitate use in the clinic, home, or other normal daily environments, the device includes a docking station 102 that is used to charge the batteries of the wearable devices 100 and download the data from each day of activities. The docking station 102 uploads the data using whatever means is available in that setting. If highspeed Internet access is available within the home, this may be used for data upload. Alternatively it permits the user to download the data to a portable storage device such as a USB thumb drive or hard drive that can then be transported to a site for final upload to the data server. If there is no simple means to download the data from the docking station 102, the data is downloaded once the docking station is returned at the end of the monitoring period. The docking station 102 requires no user intervention. The devices 100 stop recording as soon as they are docked and start recording as soon as they are undocked. According to one embodiment, the docking station 102 does not include any buttons. The docking station 102 can be connected to a computer for data extraction and processing.

B.7. Clinical Data Management and Processing Module

Once the data is uploaded to the server 104 including a clinical data management tool, the server 104 runs automatic statistical signal processing methods 106 to analyze the data and compute the results needed for the application. According to one embodiment, the system provides data for three applications: 1) human movement research, 2) movement disorders studies and clinical trials, and 3) clinical care. The system provides a simple means for researchers to conduct studies in human movement with wearable sensors 100. Study participants have an easy means of handling the devices by simply docking them when not in use. Researchers have easy, secure, and protected access to their raw sensor data through the server 104. The system also provides full support for research studies and clinical trials in movement disorders such as Parkinson's disease and essential tremor. It permits researchers to easily upload other types of data such as clinical rating scale scores, participant information, and other types of device data integrated into a secure database, and provides a means for sharing the data. Different views and controlled access permit study coordinators, research sponsors, statisticians, algorithm developers, and investigators to easily monitor the progress of studies and results. The system also provides the ability to do sequential analysis for continuous monitoring of clinical studies. According to one embodiment, the system has strict, secure, and encrypted access to any protected health information that is stored in the server. The system also supports clinical monitoring of individual patients to determine their response to therapy. This is especially helpful for movement disorders such as advanced Parkinson's in which the degree of motor impairment fluctuates continously throughout the day. As with clinical studies and trials, the server provides secure, encrypted access to patient records for authenticated care providers as well as patients themselves.

According to one embodiment, the algorithms 106 process the raw device data and extract the metrics of interest. These algorithms are insensitive to normal voluntary activities, but provide sensitive measures of the motor impairments of interest. In Parkinson's disease this may include tremor, gait, balance, dyskinesia, bradykinesia, rigidity, and overall motor state.

While particular embodiments and example results have been described, it is understood that, after learning the teachings contained in this disclosure, modifications and generalizations will be apparent to those skilled in the art without departing from the spirit of the disclosed embodiments.

The invention claimed is:

1. A wearable movement monitoring apparatus, comprising:
    (a) a sensor module comprising a plurality of low power solid state kinematics sensors, wherein said low power sensors consume less than 50 mW;
    (b) a microprocessor module comprising a low power microcontroller configured for device control, device status, and device communication;
    (c) a data storage module comprising a solid state local storage medium, said data storage module configured for sampling and storage of kinematics data at frequencies of 20 or more samples per second;
    (d) a wireless communication module comprising a low power bidirectional transceiver wherein said wireless communication module is configured for communicating and synchronizing sampling time instances of said sensor module with signals from a second apparatus; and
    (e) a power and docking module comprising a battery, an energy charging regulator circuit, and a docking connector.

2. The wearable movement monitoring apparatus of claim 1, wherein said plurality of solid state kinematics sensors include a plurality of MEMS, surface mount, low power, low noise inertial sensors including a three-axis accelerometer and a three-axis gyroscope.

3. The wearable movement monitoring apparatus of claim 2, wherein said plurality of solid state kinematics sensors further include a surface mount, low power, low noise, GMR magnetometer.

4. The wearable movement monitoring apparatus of claim 1, wherein said solid state local storage medium is substantially equivalent to a high capacity SD card configured for multi-day local storage of movement monitoring data at frequencies of 20 or more samples per second.

5. The wearable movement monitoring apparatus of claim 1, wherein said communication module is configured for communicating with a host computer while transmitting kinetic sensor data.

6. The wearable movement monitoring apparatus of claim 5, wherein said integrated antenna in said wireless communication module is a bidirectional groundplane PCB patch antenna.

7. The wearable movement monitoring apparatus of claim 6, wherein said communication module accepts transmissions from a plurality of beacons and calculates the device location.

8. The wearable movement monitoring apparatus of claim 1, wherein said power and docking module comprising said battery, said energy charging regulator circuit, and said docking connector includes an external connector to access external power and provide high speed communication with an external docking station.

9. The wearable movement monitoring apparatus of claim 8, wherein said energy charging regulator circuit is a solid state integrated circuit charger.

10. The wearable movement monitoring apparatus of claim 9, wherein said solid state integrated circuit charger is a linear Lithium Ion Polymer battery charger IC and said battery is a Lithium Ion Polymer battery.

11. The wearable movement monitoring apparatus of claim 10, wherein said Lithium Ion Polymer battery can be selected for a particular application as a function of its mAHr characteristics.

12. The wearable movement monitoring apparatus of claim 11, further comprising a module to harvest energy from the local environment.

13. The wearable movement monitoring apparatus of claim 12, wherein said module to harvest energy from the local environment comprises a kinetic generator.

14. The wearable movement monitoring apparatus of claim 13, wherein said module to harvest energy from the local environment further comprises a small solar panel.

15. The wearable movement monitoring apparatus of claim 8, wherein said docking connector provides inductive wireless power transmission for external power.

16. The wearable movement monitoring apparatus of claim 8, wherein said device status includes an action reminder chosen from the group consisting of a gentle vibration, an auditory cue, and a visual cue to remind a person to take a treatment or perform a symptom measurement task.

17. The wearable movement monitoring apparatus of claim 1, further comprising an external movement monitoring system, said system comprising:
(a) an external docking station for re-charging said wearable movement monitoring apparatus, storing movement data, and transmitting said movement data to a plurality of receiver devices, and
(b) a plurality of wireless transceiver access points for wireless transmission of said movement data to a plurality of receiver devices.

18. The wearable movement monitoring apparatus of claim 17, further comprising a web-enabled server computer including a clinical data management and analysis system for storing, sharing, analyzing, and visualizing said movement data using a plurality of statistical signal processing methods.

19. The wearable movement monitoring apparatus of claim 18, wherein said external docking station and plurality of wireless transceiver access are designed to communicate with said web-enabled server.

* * * * *